United States Patent
Neerinck et al.

(12) 
(10) Patent No.: US 6,228,471 B1
(45) Date of Patent: May 8, 2001

(54) COATING COMPRISING LAYERS OF DIAMOND LIKE CARBON AND DIAMOND LIKE NANOCOMPOSITE COMPOSITIONS

(75) Inventors: Dominique Neerinck, Hertsberge; Peter Persoone, Deinze, both of (BE)

(73) Assignee: N.V. Bekaert S.A., Zwevegem (BE)

(*) Notice: Subject to any disclaimer, the term of this patent is extended or adjusted under 35 U.S.C. 154(b) by 0 days.

(21) Appl. No.: 09/341,704
(22) PCT Filed: Jan. 23, 1998
(86) PCT No.: PCT/EP98/00527
  § 371 Date: Jul. 27, 1999
  § 102(e) Date: Jul. 27, 1999
(87) PCT Pub. No.: WO98/33948
  PCT Pub. Date: Aug. 6, 1998

(30) Foreign Application Priority Data
  Feb. 4, 1997 (EP) .................................. 97200279

(51) Int. Cl.[7] .............................. C23C 14/00; C23C 16/02
(52) U.S. Cl. ................ 428/216; 427/249; 427/255.1; 427/255.2; 427/255.3; 427/402; 427/419.1; 427/419.2; 427/569; 427/574; 427/577; 427/578; 428/212; 428/336; 428/408; 428/446; 428/697; 428/699; 428/701; 428/702
(58) Field of Search .................................. 428/446, 408, 428/216, 212, 336, 697, 699, 701, 702; 427/249, 255.1, 255.2, 255.3, 402, 419.1, 419.2, 569, 574, 577, 578

(56) References Cited
U.S. PATENT DOCUMENTS
5,352,493  10/1994  Veniamin et al. .

FOREIGN PATENT DOCUMENTS
195 44 498  6/1996  (DE) .
0 651 069  5/1995  (EP) .
97/40207  10/1997  (WO) .

OTHER PUBLICATIONS

Patent Abstacts of Japan vol. 011, No. 092 (E–491), Mar. 24, 1987 & JP 61 244068 A (Oki Electric Ind Co. LTD), Oct. 30, 1986.

Bray, et al. "New Family of Tailorable Thin–Film Coatings", Advanced Materials & Processes, Inc. Metal Progress, vol. 146, No. 6, Dec. 1, 1994 31–34, XP000473071.

*Primary Examiner*—Archene Turner
(74) *Attorney, Agent, or Firm*—Foley & Lardner

(57) ABSTRACT

The invention relates to a substrate (1) covered at least in part with a coating (6) comprising a number of layered structures (2) each such structure comprising a first diamond like nanocomposite composition layer (3) closest to the substrate, which composition comprises interpenetrating networks of a-C:H and a-Si:O, a second diamond like carbon composition layer (4) on top of said first layer, a transition layer (5) between said first and second layer comprising a mixture of said diamond like nonocomposite and said diamond like carbon compositions; and when the number of layered structures (2) is greater than one, then the coating (6) comprises an intermediate layer (7) comprising a mixture of said diamond like carbon and diamond like nanocomposite compositions sandwiched between each pair of consecutive layered structures (2).

It also relates to a process for manufacturing such a covered substrate.

24 Claims, 1 Drawing Sheet

COATING COMPRISING LAYERS OF DIAMOND LIKE CARBON AND DIAMOND LIKE NANOCOMPOSITE COMPOSITIONS

FIELD AND BACKGROUND OF THE INVENTION

The invention relates to rigid or flexible substrates covered with a thin coating of diamond-like material which thereby render the substrate surfaces i.a. very hard, corrosion and wear resistant and self-lubricating at the same time. The invention relates also to certain vacuum processes for coating the substrates.

It is generally known to coat substrates with films of diamond-like carbon. Diamond-Like Carbon (DLC) films are amorphous hydrogenated carbon films (a-C:H) that display high hardness and high elasticity combined with good corrosion protection, chemical inertness and a smooth surface. These properties make these films feasible for industrial applications such as hard, wear resistant, self lubricating and corrosion resistant coatings.

However, DLC films show several drawbacks that impede their successful commercial introduction. The most important practical problem is the difficult adhesion to several substrates, particularly steel substrates. This difficulty is caused by the high compressive residual stresses, up to several GPa, present in the material. Other disadvantages are the low thermal stability, limiting the working temperature to about 300° C., the low transmission for visible light and the increase of the coefficient of friction with increasing air humidity. Doping DLC with both metals (Ti, Zr, W, Nb, Ta) and non-metallic elements (Si, F, O, B, N) favourably influences many properties but generally lowers the hardness. Likewise, the interposition of Si, SiO or metal (Al, Ti) between the substrate and a DLC-layer, although improving its adhesion to the substrate, provides only for a soft interface.

It is also known from U.S. Pat. No. 5,352,493 to coat substrates with certain diamond-like nanocomposite compositions (DLN). Diamond-Like Nanocomposite coatings consist of an amorphous structure, comprising generally two interpenetrating networks a-C:H and a-Si:O: DLN, or Dylyn™. DLN exhibits several attractive properties when compared with Diamond-Like Carbon (a-C:H, DLC). Besides the higher temperature stability, the retaining of mechanical properties upon doping with metals and the low internal stress facilitating adhesion, the very low coefficient of friction (<0.1), often even in humid air and under water, is of prime importance for many industrial tribological applications.

However, with the present state-of-the-art deposition technology for DLN using a liquid polyphenylmethylsiloxane precursor, the hardness of the DLN coatings, as measured by depth-sensing indentation, varies generally between 12 GPa and 17 GPa. For several applications, such as abrasive applications, situations of impact erosion or severe tribological applications, this hardness value may be insufficient. In those cases, a hardness of 20 to 25 GPa may be desirable.

OBJECTS AND SUMMARY OF THE INVENTION

There is presently a high demand in the market for substrate coatings which can largely retain the favourable intrinsic properties of DLC-layers throughout the entire coating thickness and thereby avoid its drawbacks, in particular its bad adhesion to the substrates and its sensibility to compressive stresses. It is a first object of the invention to provide such improved coatings.

It is a second object of the invention to provide such coatings which have low stresses throughout their entire thickness, also for substantially thick coatings. It is a third object of the invention to provide such coatings with improved tribological properties, in particular under humid conditions. It is a further object to produce such coatings with controlled wettability or non-sticking properties (low surface energy). In this manner they can become a substitute for teflon which is very soft, or they can be used as a hard release coating in molds. It is another object to produce such coatings with controlled transparency and/or heat or electrical conductivity.

It is also an object to design and produce such coatings—in particular relatively thick coatings—in a flexible manner compared to the conventional vacuum deposition processes for DLC- or modified DLC-coatings.

According to the invention the substrate is covered, at least in part, with a multilayer coating comprising a number of layered structures each such structure comprising
- a first diamond like nanocomposite composition layer closest to the substrate, which composition comprises interpenetrating networks of a-C:H and a-Si:O,
- a second diamond like carbon composition layer on top of said first layer, and
- a transition layer between said first and second layer comprising a mixture of said diamond like nanocomposite and said diamond like carbon compositions. When the number of said layered structures is greater than one, then the coating includes an intermediate layer comprising a mixture of said diamond like carbon and diamond like nanocomposite compositions sandwiched between each pair of such consecutive layered structures.

The building up in this manner of a stack of very thin slices of DLC alternated with DLN allows indeed to deposit thicker coatings which display low stress and which thereby resist better abrasion and wear forces.

According to the invention said first layer can have a thickness of more than 0.10 and up to 3 $\mu$m. Said second layer is thinner than said first layer and has preferably a thickness of between 0.1 and 2 $\mu$m whereas said transition layer has preferably a thickness of between 0.1 and 1 $\mu$m.

Another top layer can be added which comprises a specific diamond like nanocomposite composition at its outer surface in view of controlling in addition the wettability or non-sticking properties of the top surface of said coating.

To improve further the tribological properties of the coating, the nanocomposite compositions will preferably comprise in proportion to their sum of C-, Si- and O-content in at %, 40 to 90% C, 5 to 40% Si and 5 to 25% O. To influence its conductivity, the coating can further be doped with a transition metal (of the Group IV to VII) in at least one of said first, second, transition or intermediate layers. In particular W, Zr and Ti are well suited. Any of said layers can further contain 0.5 to 5 at%, of an inert gas such as N, Ar or Kr.

A flexible process for manufacturing the covered substrate according to the invention comprises the steps of
a) depositing in a vacuum chamber said first layer starting from a continuously introduced fluid organic precursor containing the elements C, H, Si and O to be deposited in a suitable proportion, forming continuously a plasma from said precursor and depositing said composition from the plasma on the substrate to which a negative bias voltage is applied;

b) gradually exchanging said precursor by a hydrocarbon, forming continuously a plasma from the mixture of the precursor and the hydrocarbon and depositing a transition layer from said mixture in plasma form on the negatively charged substrate covered meanwhile with the diamond like nanocomposite composition whereby said mixture composition gradually changes from a diamond like nano-composite composition to a diamond like carbon composition;

c) continuing the plasma deposition of the diamond like carbon composition layer from said hydrocarbon and, when more than one layered structure has to be deposited, then per deposition of another such layered structure;

d) firstly gradually exchanging said hydrocarbon from step c by a suitable organic precursor, forming continuously a plasma from the mixture of the hydrocarbon and said precursor and depositing an intermediate layer from said mixture in plasma form on the negatively charged substrate covered meanwhile with the previous structure whereby said mixture composition gradually changes from a diamond like carbon composition to a diamond like nanocomposite composition and e) secondly repeating te steps a to c.

This process is quite easy to monitor since changes in only two material flows (precursor and hydrocarbon) have to be kept under control. After all, instead of using Si or a metal bridge layer between a DLC-layer and the substrate (according to the state of the art), the application of DLN-layers in the stack which alternate with DLC-layers provides a reasonably hard and wear resistant coating with good adhesion. The necessity is thereby avoided of having to deposit a thick DLC-layer on said bridge layer.

The liquid organic precursor is preferably a siloxane such as hexamethyldisiloxane (with a relatively high content of Si and O) or a polyphenylmethylsiloxane (with a lower content of Si and O). The hydrocarbon is preferably an aliphatic saturated or unsaturated hydrocarbon gas from the series C1 to C5, such as etylene. acetylene, propane, butane, cyclopentane. It can also be an aromatic hydrocarbon liquid. such as benzene or a substituted benzene. The higher the molecular weight of the hydrocarbon, the higher the deposition rate.

To increase the deposition rate a stimulated plasma can be applied in step a) to e), using electron emission from a hot filament. This stimulated plasma comprises eg. an electron assisted DC-discharge using a filament with a filament current of 50–150 A. a negative filament DC bias voltage of 50–300 V and a plasma current between 0.1 and 20 A as described in applicant's copending European patent application No. 96201070.8. This thermionic electron emission from a hot filament is used to sustain the plasma at low pressures or to increase the plasma density.

In view of the production of DLN-layers in step a) with a composition comprising $0.4<C/C+Si+O<0.9$ and $0.05<Si/C+Si+O<0.4$ and $0.05<O/C+Si+O<0.25$. a negative DC-bias or negative RF self-bias voltage of 200 to 1200 V is preferably applied to the substrate in order to attractions formed in the plasma. The frequency of the RF-voltage is thereby quite low: between 30 and 1000 kHz as described in applicant's copending European patent application No. 96201070.8. For the deposition of the diamond like carbon composition layers a negative bias voltage is applied of 150 to 800 V to the substrate in order to attract ions formed in the plasma. When hexamethylsiloxane is used as a precursor the proportions of Si and O in the DLN can even be higher.

This will favour the non-wettability or non-sticking behaviour of the coating, in particular with a DLN-layer at its top surface.

During any of the steps a to e, an inert gas can be introduced in the vacuum chamber, ionised and incorporated by ion bombardment of the growing layer. As a result the nanohardness of the deposited film may increase. This gas can be introduced separately or as a carrier gas for the liquid siloxane precursor. In the latter case it enables an easy evaporation of the precursor as will be described below. This favours the stability and reproducibility of the deposition process. By admitting this gas, the operating pressure rises to $10^{-3}$–$10^{-2}$ mbar. This favours a homogeneous deposition eg, also on substrates with a complex shape.

When a hydrocarbon gas is used as or added to the inert carrier gas. the C-content of the deposited layer can be influenced as well. If desired, during any of the steps a to e, at least one transition metal can be codeposited by ion sputtering or by thermal evaporation to fine tune i.a. the conductivity of the coating.

DETAILED DESCRIPTION

Figure 1:
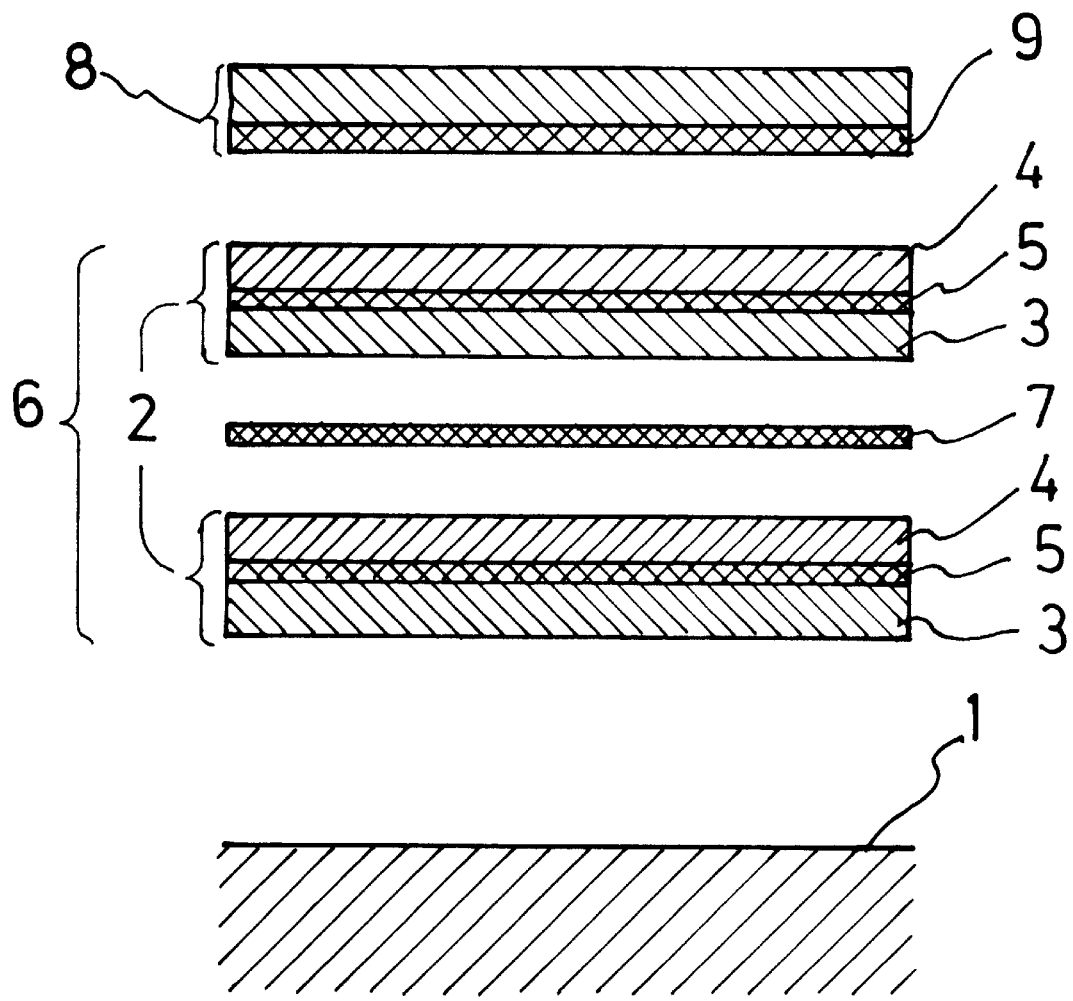
FIG. 1 shows an exploded view of the arrangement of a possible stack of different layers building up the coating on a substrate.

As shown in FIG. 1. the arrangement of the different layers on the substrate 1 is as follows. The coating 6 comprises two layered structures 2 each such structure comprising a first diamond like nanocomposite composition layer 3 closest to the substrate, which composition comprises interpenetrating networks of a-C:H and a-Si:O. a second diamond like carbon composition layer 4 on top of said first layer and a transition layer 5 between said first and second layer comprising a mixture of said diamond like nanocomposite and said diamond like carbon compositions.

Sandwiched between the two layered structures 2 the coating 6 includes an intermediate bonding layer 7 comprising a mixture of said diamond like carbon and diamond like nanocomposite compositions.

On top of the outermost layered structure 2 a top layer 8 can be present which comprises a diamond like nanocomposite composition at its outer surface and a sublayer 9 comprising again a mixture of DLC and DLN to secure a good bond to the layered structure 2 in contact therewith.

The deposition of a bilayer stack will now be described as an exemplary embodiment of the invention. With a bilayer stack is meant one layered structure 2 comprising the first layer 3. second layer 4 and interlayer 5 as defined above. In a vacuum reactor as described in the copending application mentioned hereinbefore hexamethyldisiloxane is introduced with Ar as a carrier gas. The mixture gas/precursor is in fact delivered in a controllable manner to the vacuum chamber through a controlled evaporation mixing system. The liquid siloxane is passed through a liquid mass flow controller to a mixing valve where it is combined with the carrier gas stream. From there it is transferred to a mixing chamber which is heated to about 80° C. to 200° C. The siloxane evaporates in the mixture and the hot mixture enters the vacuum chamber whereby the pressure in the chamber rises to between $10^{-3}$ and $10^{-2}$ mbar. The deposition rate is about 2 $\mu$m per hour. This is much higher than with the introduction of a polyphenylmethylsiloxane through a porous body and without a carrier gas.

Precursors with a high content of Si and O such as tetraethylortosilicate or hexamethyldisiloxane can result in a DLN-layer with a Si/C+O+Si up to about 36% and a O/C+O+Si up to about 17%. After a thickness has been reached of eg. 1 μm. the flow of the siloxane is gradually reduced to a zero value. At the same time methane is introduced and the transition layer 5 is formed with a thickness of between 0.1 and 0.5 μm. The pressure in the chamber rises thereby up to about $5.10^{-3}$ mbar.

The simultaneous introduction of gases into the chamber during the deposition of DLN. has the advantage of providing an easy way of changing the composition of the deposited layer. The Si or O content in the DLN layer can be lowered by adding a specific flow of C-containing gas. thereby increasing the relative content of C eg, in the transition layer 5. Changing the composition of the DLN layer by changing during deposition the composition of the liquid precursor is more difficult and certainly less instantaneous. In principle, the possibility of easily changing and adapting the gas flow compositions entering the vacuum chamber renders the process extremely flexibel and allows for the production of any desirable gradient in the composition throughout the thickness of the coating.

The further deposition of DLC from the methane precursor continues thereafter in view of building the DLC top layer 4 with a thickness of typically 0.5 to 1 μm or even up to 2 μm. This layer provides the coating with the required hardness. improved abrasion and scratch resistance. The top DLC layer also ensures surface biocompatibility of the deposit (and may for some applications eliminate extended investigations on the biocompatibility of DLN compositions).

It is also desirable to subject the substrate to a reactive ion etching (RIE) step before depositing the DLN-layer in step a. This can be done by a bombardment of the substrate by ions of an inert gas such as Ar. The surface is thereby activated and residual oxides are removed from said surface.

Applying DLC as a top layer has the advantage that the deposition run can be instantaneously stopped by shutting down the gas flow, while for ending a pure DLN deposition without carrier gas (eg. by introducing the polyphenylmethylsiloxane precursor through a porous body), 10 to 15 minutes at a low deposition rate are needed because of the ongoing evaporation of remaining liquid precursor.

The provision of the bilayer structure however enables a good adhesion to the substrate which is demonstrated by favourable results from a scratch test for adhesion assessment. In this test, the coated substrate is loaded with a Rockwell indenter with a 200 μm tip radius. The load is gradually increased while moving the tip laterally over the coating surface. The place where cracks or delamination appear is an indication of the normal load at which failure of the coating occurs. In the following test, we only consider the critical load (in N) to be reached when the first delamination of the coating takes place. The scratch experiments are all performed on high-speed M2 steel. having a hardness of 10–12 GPa, since the critical load also depends on the substrate hardness.

The manifold published difficulty of adhesion of hard DLC films was demonstrated in our process by depositing DLC directly on steel substrates, using a methane gas precursor. These coatings, deposited on stainless steel 304 and M2 steel substrates, delaminated spontaneously upon removing them from the deposition chamber. On the contrary. DLN films deposited using the process described in the copending patent cited above, exhibit excellent adhesion manifested by a critical load of 25 to 40 N in the scratch test.

When during the deposition of the top DLC layer a substrate DC self-bias of 150 to 800 V is applied, the DLN/DLC bilayers have a nanohardness of 17 to 20 GPa. These nanohardness values are obtained through a nanoindentation test for determination of the wear resistance. In the scratch test, these DLN/DLC bilayers reveal a critical load of 25 to 35 N, similar to pure DLN films.

The DLN/DLC bilayers thus succeed in combining the good adhesion of pure DLN films and the higher hardness value of pure DLN films. This unique combination of industrially attractive properties opens up many tribological applications of these coating structures. Standard ball-on-disk experiments have been performed on these DLN/DLC bilayers using a 100Cr6 steel ¼" bearing ball as counterbody with a 10 N normal load, in air of approximately 50% RH and a linear velocity of 0.17 m/s. The experiment was carried out for 100000 cycles after which the wear factor was determined using profilometric measurements of the wear track. For pure DLN films, wear factors of $2 \times 10^{-7}$ $mm^3/Nm$ are obtained, while for DLN/DLC bilayers a wear factor of $0.5 \times 10^7$ $mm^3/Nm$ has been reached, despite the fact that the coefficient of friction of DLN/DLC bilayers is slighly higher (about 0.1) than the coefficient of friction of pure DLN (about 0.06). Therefore, DLN/DLC bilayers are an excellent candidate for low-wear sliding applications.

In conclusion, DLN layers can be considered as the ultimate adhesion-promoting underlayer for DLC films. increasing the adhesion to critical loads above 30 N. Other adhesion-promoting underlayers such as Si. SiC or metal layers have often been used for DLC films, but rarely these high critical loads have been reached. A DLN underlayer has the additional advantage that the DLN layer on itself already provides a reasonably good wear resistance due to its hardness of 1215 GPa, which is higher than Si or metal layers.

For applications requiring both high hardness and low friction (<0.1). another structural combination of DLN and DLC can be proposed. The low-friction properties of DLN coatings, in normal and humid air and under water, are most probably caused by the specific nature of the transfer layer deposited on the steel counterbody in a ball-on-disk experiment. This transfer layer has been observed on the steel ball after several experiments with DLN coatings, although detailed structural investigations of the transfer layer are still ongoing. Transfer layers have frequently been observed on the counterbody in ball-on-disk experiments with DLC or doped DLC coatings. To obtain low friction in a tribological application, a transfer layer should be able to be built up on the surface of the sliding partner. Therefore, a top DLN layer should be applied.

The ideal structure providing a combination of hardness and low-friction may be a DLN/DLC multilayer comprising a stack 6 built up of a series of layered structures 2 with intermediate layers 7 and finally covered with a toplayer 8, having a DLN outer surface and a bonding sublayer 9. On the one hand the alternation of DLN-layers 3 and DLC-layers 4 solves the internal stress and adhesion problem for thick layerstacks. On the other hand the provision of DLN at the top surface (layer 8) produces a low friction coefficient and a low surface energy (low contact angle). To control this surface energy properly, the Si- and O-content in the outer surface can be adjusted. An increase in Si and O will thereby increase the contact angle and thereby generally also improve the coating's aptitude as a release or non-sticking coating or as a barrier layer against humidity. An average increase of Si- and O- content in the stack may further improve its overall optical transparency. In the multilayer stack the total number of layers 3, (respectively 4) may range between 3 and 25, and preferably between 5 and 10.

The bilayer or multilayer stack according to the invention can be used in a great number of applications. Their composition can be adjusted specifically to meet preset requirements for products having surfaces with low friction, high hardness, abrasion and wear resistance. corrosion resistance and nonsticking properties (high contact angle versus certain liquids, gases or even solids). The stacked coating can thus be used as surface layer in certain cutting tools for eg. paper and textiles or in metal working tools eg, for shaping aluminium workpieces. The coating can serve as a low friction agent for biomedical prosthesis eg, for hip and knee joint replacement. It can be used as release coating for shaping molds for plastics (press molding, injection molding) for deep drawing dies and stamping of tablets and capsules for the pharmaceutical, food and other chemical industries and on sealing elements (eg. plastic sealing bars).

Low wear and low friction coatings according to the invention can be applied in alumina water tap valves and on all kinds of sliding elements and friction parts in textile machines and in automotive. food and pharmaceutical industry to replace lubricants (eg, bearings, pistons and gears).

The DLN/DLC coating stacks are in particular useful as release coatings in high precision stamping or molding devices for tablets and capsules since they may allow the deletion of lipophyle or hydrophyle lubricants such as magnesium- or zinc stearate, respectively natriumbenzoate, boric acid, leucine etc. Besides tablets for medicinal use, the DLN/DLC release coatings are also applied for preparing tablets in molds for chocolates, sweets, for detergent powders, for effervescent tablets and even for tablets containing metal powder.

What is claimed is:

1. A substrate (1) covered at least in part with a coating (6) comprising a number of layered structures (2) each such structure comprising
    a first diamond like nanocomposite composition layer (3) closest to the substrate, which composition comprises interpenetrating networks of a-C:H and a-Si:O,
    a second diamond like carbon composition layer (4) on top of said first layer,
    a transition layer (5) between said first and second layer comprising a mixture of said diamond like nanocomposite and said diamond like carbon compositions; and
when the number of layered structures (2) is greater than one, then the coating (6) comprises an intermediate layer (7) comprising a mixture of said diamond like carbon and diamond like nanocomposite compositions sandwiched between each pair of consecutive layered structures (2).

2. A substrate according to claim 1 wherein said first layer (3) has a thickness of more than 0.1 and up to 3 µm.

3. A substrate according to claim 2 wherein said second layer (4) is thinner than said first layer and has a thickness of between 0.1 and 2 µm.

4. A substrate according to claim 1 whereby the transition layer (5) has a thickness of between 0.1 and 1 µm.

5. A substrate according to claim 1 having on top of said coating (6) a top layer (8) comprising a diamond like nanocomposite composition at its outer surface.

6. A substrate according to claim 1 wherein the nanoposite composition comprises in proportion to the sum of C, Si and O in at %, 40 to 90% C, 5 to 40% Si and 5 to 25% O.

7. A substrate according to claim 1 wherein at least one of said first, second, transition or intermediate layers is further doped with a transition metal.

8. A substrate according to claim 1 wherein at least one of said first, second, transition or intermediate layers contains 0.5 to 5 at % of an inert gas.

9. A process for manufacturing a covered substrate (1) according to claim 1 comprising the steps of
    a) depositing in a vacuum chamber said first layer (3) starting from a continuously introduced fluid organic precursor containing the elements C, H, Si and O to be deposited in a suitable proportion, forming continuously a plasma from said precursor and depositing said composition from the plasma on the substrate to which a negative bias voltage is applied;
    b) gradually exchanging said precursor by a hydrocarbon, forming continuously a plasma from the mixture of the precursor and the hydrocarbon and depositing a transition layer (5) from said mixture in plasma form on the negatively charged substrate covered meanwhile with the diamond like nanocomposite composition (3) whereby said mixture composition gradually changes from a diamond like nanocomposite composition to a diamond like carbon composition;
    c) continuing the plasma deposition of the diamond like carbon composition layer (4) from a hydrocarbon and, when more than one layered structure (2) has to be deposited, then per deposition of another such layered structure;
    d) firstly gradually exchanging said hydrocarbon from step c by a suitable organic precursor, forming continuously a plasma from the mixture of the hydrocarbon and said precursor and depositing an intermediate layer (7) from said mixture in plasma form on the negatively charged substrate covered meanwhile with the previous structure (2) whereby said mixture composition gradually changes from a diamond like carbon composition to a diamond like nanocomposite composition; and
    e) secondly repeating te steps a to c.

10. A process according to claim 9 wherein the liquid organic precursor is a siloxane.

11. A process according to claim 10, wherein said siloxane is a hexamethyldisiloxane.

12. A process according to claim 9 wherein the hydrocarbon is an aliphatic hydrocarbon gas from the series C1 to C5.

13. A process according to claim 9 wherein the hydrocarbon is an aromatic hydrocarbon liquid.

14. A process according to claim 13 wherein the liquid is benzene or a substituted benzene.

15. A process according to claim 9 whereby the plasma is a stimulated plasma using electron emission from a hot filament.

16. A process according to claim 15 whereby the stimulated plasma deposition comprises an electron assisted DC-discharge using a filament with a filament current of 50–150 A, a negative filament DC bias voltage of 50–300 V and a plasma current between 0.1 and 20 A.

17. A process according to claim 15 whereby, for the deposition of the nanocomposite composition layers on the substrate, a negative DC-bias or negative RF self-bias voltage of 200 to 1200 V is applied to it, and for the deposition of the diamond like carbon composition layers a negative self-bias voltage of 150 to 800 V is applied to the substrate in order to attractions from the plasma.

18. A process according to claim 9 whereby, for the deposition of the nanocomposite composition layers on the substrate, a negative DC-bias or negative RF self-bias voltage of 200 to 1200 V is applied to it, and for the deposition of the diamond like carbon composition layers a negative self bias voltage of 150 to 800 V is applied to the substrate in order to attract ions from the plasma.

19. A process according to claim 18 wherein the frequency of the RF-voltage is between 30 and 1000 kHz.

20. A process according to claim 9 whereby, during any of the steps a to e, an inert gas is introduced in the vacuum chamber, ionised and incorporated by ion bombardment of the growing layer.

21. A process according to claim 9 wherein for the deposition of the diamond like nanocomposite compositions, the siloxane precursor is mixed with a carrier gas for introduction in the vacuum chamber and the mixture is heated to evaporate the precursor.

22. A process according to claim 21 wherein the carrier gas comprises an inert gas and/or a hydrocarbon gas.

23. A process according to claim 9 whereby, during any of the steps a to e, at least one transition metal is codeposited by ion sputtering or by thermal evaporation.

24. A process according to claim 9 whereby, before carrying out the step a, the substrate is plasma etched by a bombardment of ions of an inert gas.

* * * * *